(12) United States Patent
Vincent et al.

(10) Patent No.: US 11,547,846 B2
(45) Date of Patent: Jan. 10, 2023

(54) PUMP-VALVING ASSEMBLY FOR A PULSATILE FLUID PUMP

(71) Applicant: VentriFlo, Inc., Pelham, MA (US)

(72) Inventors: Douglas E. Vincent, Pelham, NH (US); George Koenig, Nashua, NH (US); Matthew J. Murphy, Marshfield, MA (US)

(73) Assignee: VentriFlo, Inc., Pelham, NH (US)

( * ) Notice: Subject to any disclaimer, the term of this patent is extended or adjusted under 35 U.S.C. 154(b) by 0 days.

(21) Appl. No.: 17/182,915

(22) Filed: Feb. 23, 2021

(65) Prior Publication Data
US 2022/0265994 A1 Aug. 25, 2022

(51) Int. Cl.
*A61M 60/424* (2021.01)
*F04B 17/00* (2006.01)
(Continued)

(52) U.S. Cl.
CPC ........ *A61M 60/424* (2021.01); *A61M 60/894* (2021.01); *F04B 15/02* (2013.01);
(Continued)

(58) Field of Classification Search
CPC .............. A61M 60/268; A61M 60/894; A61M 2230/04; A61M 60/562; A61M 60/00;
(Continued)

(56) References Cited

U.S. PATENT DOCUMENTS 3,741,243 A * 6/1973 Deibler .................. F16K 15/04
137/528
3,794,291 A * 2/1974 Suyama ................ F16K 5/0673
251/171
(Continued)

FOREIGN PATENT DOCUMENTS

FR 2309206 A1 11/1976
WO 9836792 A1 8/1998

OTHER PUBLICATIONS

International Searching Authority—International Search Report, pertaining to International Application No. PCT/US2021/019238, dated Oct. 15, 2021, together with the Written Opinion of the International Searching Authority, 10 pages.

*Primary Examiner* — Dominick L Plakkoottam
(74) *Attorney, Agent, or Firm* — Sunstein LLP (57) ABSTRACT

A pump-valving assembly for a pulsatile fluid pump includes a pumping chamber, an inlet port, and an outlet port. The pump-valving assembly further includes an inlet ball check-valve assembly, first and second tapered tracts disposed between the inlet port and the pumping chamber, an outlet ball check-valve assembly, and third and fourth tapered tracts disposed between the pumping chamber and outlet port. The first tapered tract expands in cross sectional area from the inlet port to the inlet ball check valve assembly, and the second tapered tract decreases in cross sectional area from the inlet ball check valve assembly to the chamber. The third tapered tract expands in cross sectional area from the chamber to the outlet ball check valve assembly and the fourth tapered tract decreases in cross sectional area from the outlet ball check valve assembly to the outlet port.

5 Claims, 11 Drawing Sheets

(51) Int. Cl.
 *F04B 15/02* (2006.01)
 *F04B 53/10* (2006.01)
 *A61M 60/894* (2021.01)
 *A61M 60/268* (2021.01)

(52) U.S. Cl.
 CPC .............. *F04B 17/00* (2013.01); *F04B 53/10* (2013.01); *A61M 60/268* (2021.01)

(58) Field of Classification Search
 CPC .......... A61M 60/258; A61M 2202/047; A61M 5/14224; A61M 60/274; A61M 60/279; A61M 60/833; F04B 17/00; F04B 43/04; F04B 43/06; F04B 53/10; F04B 7/00
 See application file for complete search history.

(56) References Cited

U.S. PATENT DOCUMENTS

| | | | | |
|---|---|---|---|---|
| 4,594,058 A * | 6/1986 | Fischell | ............ | A61M 5/16809 417/413.1 |
| 5,300,111 A * | 4/1994 | Panton | ................. | A61M 60/40 623/3.19 |
| 5,507,194 A * | 4/1996 | Scavuzzo | ................. | G01N 1/12 73/864.63 |
| 5,635,079 A * | 6/1997 | Becking, II | ............. | C02F 1/003 210/266 |
| 5,916,191 A * | 6/1999 | Plunkett | .............. | A61M 60/562 604/6.11 |
| 6,293,901 B1 * | 9/2001 | Prem | ...................... | F04D 29/048 600/17 |
| 7,029,245 B2 * | 4/2006 | Maianti | ............... | A61M 1/1698 417/395 |
| 7,238,165 B2 * | 7/2007 | Vincent | ............... | A61M 60/148 604/6.11 |
| 7,850,593 B2 * | 12/2010 | Vincent | ............... | A61M 60/148 600/16 |
| 9,234,514 B2 * | 1/2016 | Jones | .................... | F04B 43/026 |
| 10,722,628 B2 * | 7/2020 | Azzolina | ............. | A61M 60/894 |
| 10,871,157 B2 * | 12/2020 | Tracey | ...................... | G01K 1/16 |
| 10,989,320 B2 * | 4/2021 | Dercher | ................ | F16K 15/063 |
| 2004/0116769 A1 * | 6/2004 | Jassawalla | ........... | A61M 60/40 600/16 |
| 2007/0255089 A1 | 11/2007 | Vincent et al. | | |
| 2008/0008609 A1 * | 1/2008 | Pate | ........................ | F04B 17/00 417/415 |
| 2010/0038362 A1 * | 2/2010 | Sasaki | ................... | F16K 5/0631 220/88.3 |
| 2012/0032501 A1 * | 2/2012 | Lalone | ................. | B60T 17/043 303/9.76 |
| 2015/0047721 A1 * | 2/2015 | Hayles | .................... | F16K 15/04 137/528 |
| 2020/0208503 A1 | 7/2020 | Dyck et al. | | |

* cited by examiner

PUMP-VALVING ASSEMBLY FOR A PULSATILE FLUID PUMP

RELATED APPLICATIONS

The present application is one of four applications being filed on the same day and bearing Ser. Nos. 17/182,915, 17/182,893, 17/103,067, and 17/183,090. Each of these related applications, other than the present application, is hereby incorporated herein by reference in its entirety.

Technical Field

The present invention relates to pulsatile fluid pumps, and more particularly to pulsatile fluid pumps suitable for pumping blood.

BACKGROUND ART

A pulsatile fluid pump is taught in U.S. Pat. No. 7,850,593 ("our prior patent") for an invention of Douglas Vincent and Matthew Murphy, who are co-inventors of the present invention. Our prior patent discloses a pump actuated by a linear motor configured to cause reciprocation of a flexible membrane, serving as a wall of a fluid housing, that is in turn coupled to a pair of ball valves, in a manner as to implement pulsatile fluid flow.

SUMMARY OF THE EMBODIMENTS

In accordance with one embodiment of the invention, a pump-valving assembly for a pulsatile fluid pump includes a generally cylindrical pumping chamber, an inlet port having an entrance and coupled to the pumping chamber, and an outlet port having an exit and coupled to the pumping chamber. The pump-valving assembly further includes a spherically shaped inlet ball check-valve assembly coupled to the inlet port, first and second tapered tracts coupled to the inlet ball check-valve assembly and disposed between the inlet port and the pumping chamber respectively, a spherically shaped outlet ball check-valve assembly coupled to the outlet port, and third and fourth tapered tracts coupled to the outlet ball check-valve assembly and disposed between the pumping chamber and outlet port respectively. The first tapered tract expands in cross sectional area from the entrance to the inlet port to the inlet ball check valve assembly, and the second tapered tract decreases in cross sectional area from the inlet ball check valve assembly to the chamber, and the inlet ball check valve assembly gates flow between the pumping chamber and the inlet port. Further, the third tapered tract expands in cross sectional area from the chamber to the outlet ball check valve assembly and the fourth tapered tract decreases in cross sectional area from the outlet ball check valve assembly to the exit from the outlet port and the outlet ball check valve assembly gates flow between the pumping chamber and the outlet port.

Alternatively, or in addition, a taper of at least one of the tapered tracts is conical. Also, alternatively or in addition, the pump-valving assembly further includes an inflow transition region, coupled between the second tapered tract and the chamber, configured to conduct fluid along a path that is roughly tangential to an internal circumference of the chamber, so as to smoothly establish fluid flow in the chamber.

Alternatively, or in addition, the pump-valving assembly further includes an outflow transition region, coupled between the chamber and the third tapered tract, providing a channel, beginning in the chamber, of gradually increasing width, the outflow transition region configured to allow fluid to smoothly exit from fluid rotation in the chamber to linear flow in the third tapered tract.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Definitions. As used in this description and the accompanying claims, the following terms shall have the meanings indicated, unless the context otherwise requires:

"Normal flow" is flow from the entrance to the inlet port 111 through the chamber 102 to the exit of the outlet port 121.

A "slight reversal of flow" past a ball in a ball check valve is a small, controlled amount of desired reverse flow past the ball before the ball is seated in a closed position.

"Diastole mode" is a phase of operation of a pulsatile pump, according to embodiments of the present invention, during which the diaphragm (not shown) of the pump-valving assembly 101 is pulled away from the chamber 102 so as to create negative pressure within the chamber 102, inlet ball check valve assembly 110, and third tapered tract 126, but not the fourth tapered tract 122.

"Systole mode" is a phase of operation of a pulsatile pump, according to embodiments of the present invention, during which the diaphragm (not shown) is pushed towards the chamber 102, so as to create positive pressure within the chamber 102, outlet ball check valve assembly 120, and the second tapered tract 116, but not the first tapered tract 112.

Figure 1:
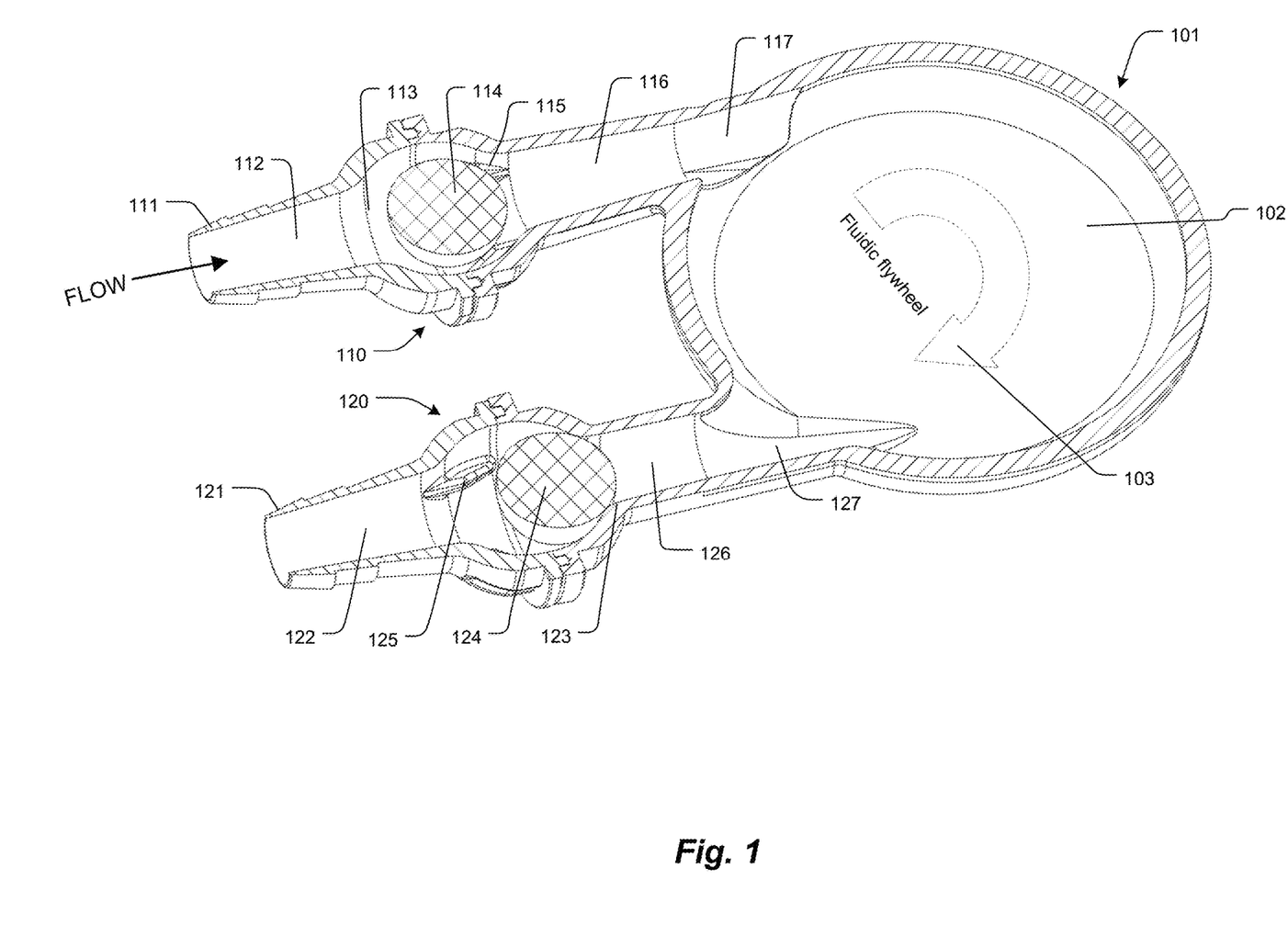
FIG. 1 is a horizontal section of a pump-valving assembly 101 in accordance with an embodiment of the present invention, wherein the pump-valving assembly 101 is in diastole mode in which the chamber 102 is being filled.

FIG. 1 is a horizontal section of a pump-valving assembly 101 in accordance with an embodiment of the present invention, wherein the pump-valving assembly 101 is in diastole mode in which the chamber 102 is being filled. Fluid flows into the inlet port 111, through the first tapered tract 112, past the inlet ball 114, as that inlet ball 114 engages against the inlet ribs 115 that create gaps between the inlet ball 114 and the second tapered tract 116 that allow fluid to flow into the second tapered tract 116 and then into the chamber 102. The pump-valving assembly 101 operates in cooperation with a diaphragm (not shown) that seats around the circumference of the chamber 102. The motion of the diaphragm in cooperation with the inlet ball check valve assembly 110 and the outlet ball check valve assembly 120 causes the flow of fluid into the chamber 102. While the chamber 102 is filling, the outlet ball 124 in the outlet ball check valve assembly 120 settles against the outlet seat 123 to prevent fluid flow from the outlet port 121 back into the chamber 102. The fluidic flywheel 103 (described later) is illustrated. (In these figures, like numbered items correspond to similar components across different figures.)

Figure 2:
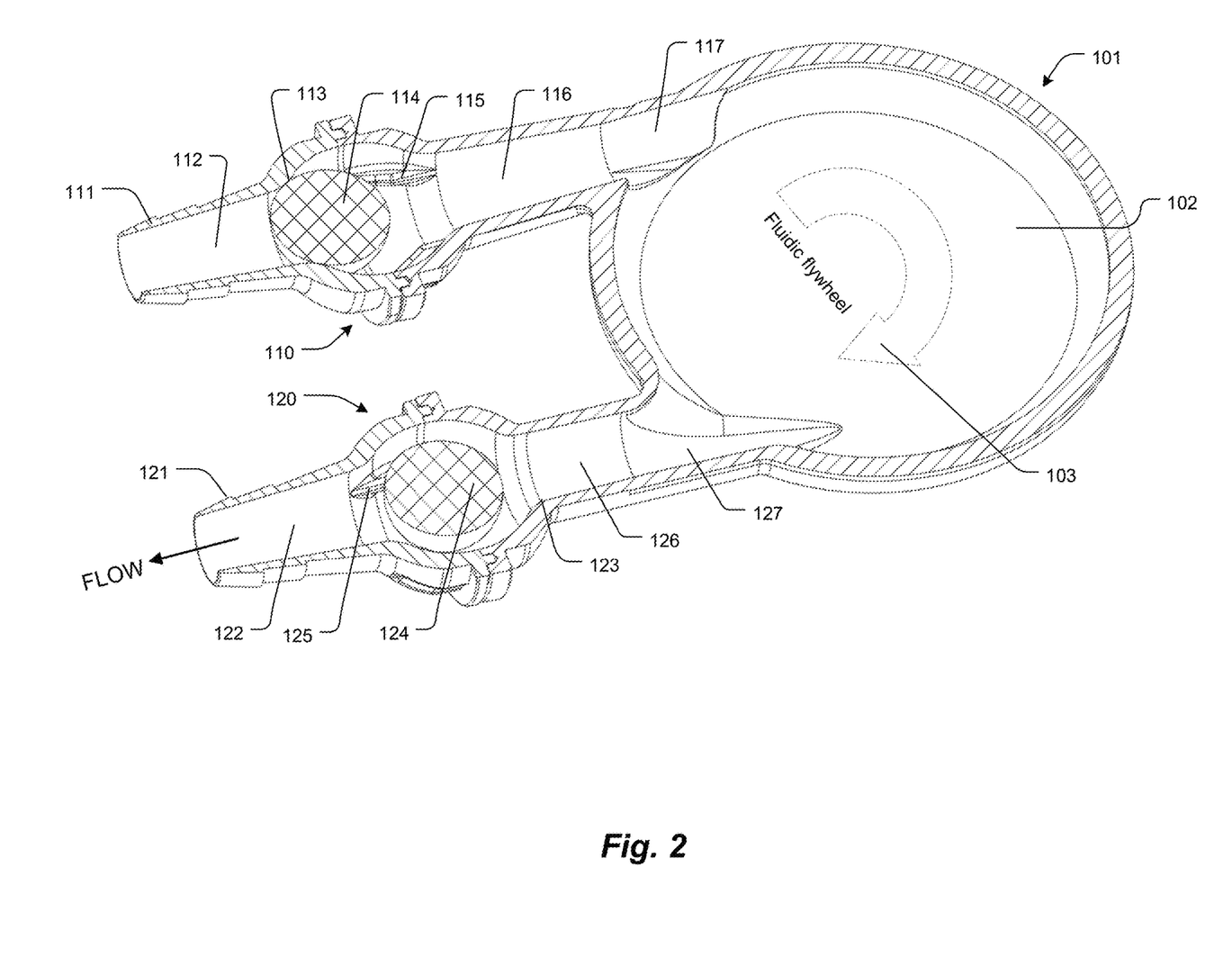
FIG. 2 is a horizontal section of the pump-valving assembly 101 of FIG. 1, wherein the pump-valving assembly 101 is in systole mode in which the chamber 102 is being emptied.

FIG. 2 is a horizontal section of the pump-valving assembly 101 of FIG. 1, wherein the pump-valving assembly 101 is in systole mode in which the chamber 102 is being emptied. The outlet port 121 receives fluid from the chamber 102 via the third tapered tract 126, past the outlet ball 124 as that outlet ball 124 engages against the outlet ribs 125 that create gaps between the outlet ball 124 and the fourth tapered tract 122 that allow fluid to flow into the fourth tapered tract 122 and then exit the outlet port 121. The pump-valving assembly 101 operates in cooperation with a diaphragm (not shown) that seats around the circumference of the chamber 102. The motion of the diaphragm in cooperation with the inlet ball check valve assembly 110 and the outlet ball check valve assembly 120 causes flow of the fluid out of the chamber 102. While the chamber 102 is emptying, the inlet ball 114 in the inlet ball check valve assembly 110 settles against inlet seat 113 to prevent fluid flow from the chamber 102 back into the inlet port 111. The fluidic flywheel 103 (described later) is illustrated.

Figure 3:
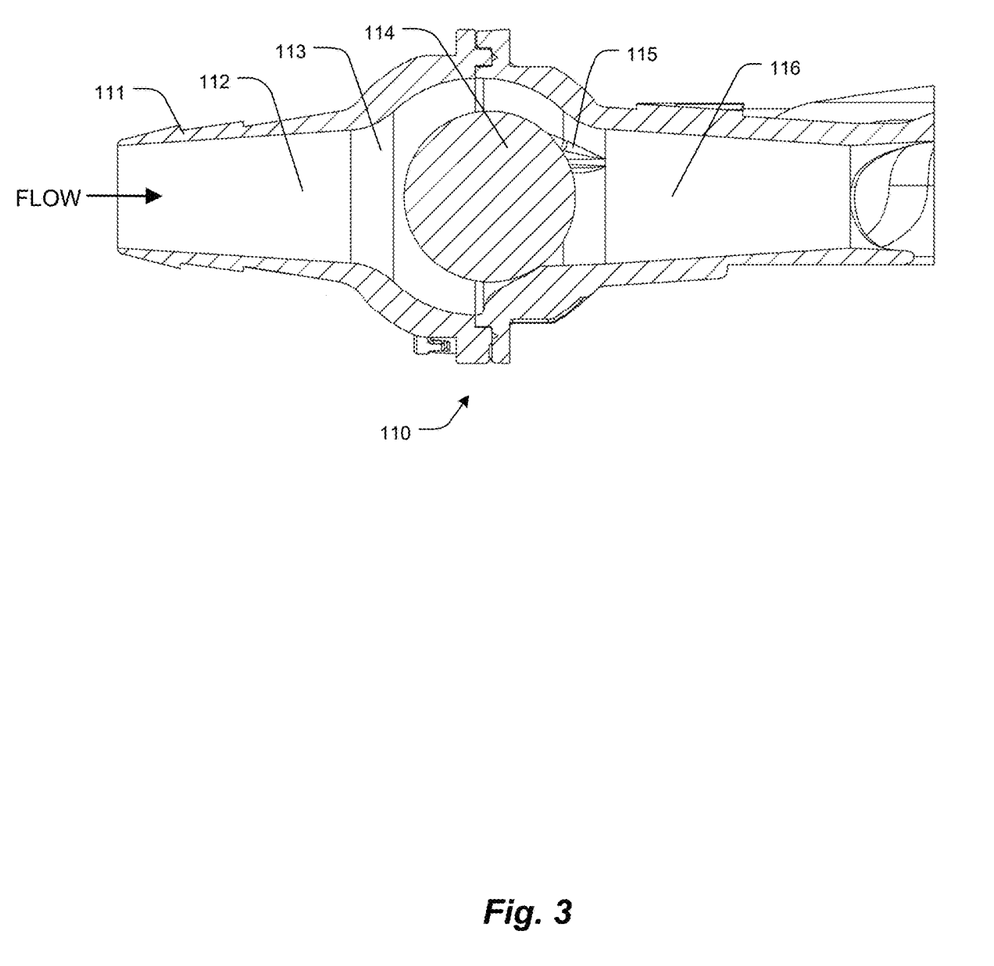
FIG. 3 is a vertical section of the inlet ball check valve assembly 110 of the embodiment of FIG. 1 wherein the pump-valving assembly 101 is in diastole mode in which the chamber 102 is being filled and the inlet ball 114 is in the filling position.

FIG. 3 is a vertical section of the inlet ball check valve assembly 110 of the embodiment of FIG. 1 wherein the pump-valving assembly 101 is in diastole mode in which the chamber 102 is being filled and the inlet ball 114 is in the filling position. The negative pressure created by the diaphragm (not shown) pulling away from the chamber 102 as it is filling causes fluid to flow into the inlet port 111, through the first tapered tract 112, past the inlet ball 114, as that inlet ball 114 engages against the inlet ribs 115, there result gaps between the inlet ball 114 and the second tapered tract 116, so as to allow fluid to flow into the second tapered tract 116 and then into the chamber 102.

Fluid flow in the tapered tracts 112, 116, 122, and 126 provides a gradual change in velocity as a function of cross-sectional area to maintain continuity of flow leading up to and past each of the balls 114 and 124. Embodiments of the invention include a spherically shaped inlet ball check-valve assembly coupled to the inlet port through a first tapered tract and to the pumping chamber through a second tapered tract, the inlet ball check-valve assembly having an interior wall defining a spherical volume in which a discrete inlet ball is disposed, the assembly including an inlet valve seat and a ribbed inlet ball retaining region. Similarly, these embodiments include a spherically shaped outlet ball check-valve assembly coupled to the pumping chamber through a third tapered tract and to the outlet port through a fourth tapered tract, the outlet ball check-valve assembly having an interior wall defining a spherical volume in which a discrete outlet ball is disposed, the assembly including an outlet valve seat and a ribbed outlet ball retaining region. The first tapered tract expands in cross sectional area from the entrance to the inlet port to the inlet ball check valve assembly, and the second tapered tract decreases in cross sectional area from the inlet ball check valve assembly to the chamber. The inlet ball check valve assembly gates flow between the pumping chamber and the inlet port. The third tapered tract expands in cross sectional area from the chamber to the outlet ball check valve assembly, and the fourth tapered tract decreases in cross sectional area from the outlet ball check valve assembly to the exit from the outlet port. The outlet ball check valve assembly gates flow between the pumping chamber and the outlet port. For either ball 114 or 124, the ball geometry, the physical properties of the ball, and the ball check-valve assembly as a whole are configured to stabilize the ball in successive positions and transitions to these positions, as well as the velocity of the ball, as these things are modulated in the course of pulsatile flow of fluid through the pump—over the ranges of viscosity for blood or other fluids being pumped. In the course of pumping, the pulsatile nature of the pump causes a change in direction of flow over the balls; the pump is configured to achieve this change in direction in a manner that minimizes the total pressure loss across the ball check valve assembly. Additionally, when a given one of the balls has moved to an open position (against the ribs 115 or 125, as the case may be) enabling flow past the given ball, the pump is configured to maintain sufficient flow velocity (and differential pressure across the given ball) to cause it to be retained against the ribs. Similarly, the check valve assembly is configured to create symmetry of other fluid velocity forces on the given ball to prevent unwanted lateral motion of the given ball The ribs 115 and 125 occupy a portion of the volume of the ball check valve assembly 110 or 120 in which they are located. That volume displaced by these ribs 115 or 125 therefore reduces the cross-sectional area of the ball check valve assembly 110 or 120 in the vicinity of the ribs 115 or 125 and thus causes an increase in velocity of fluid flow in the region. We utilize this increased velocity, as described in the previous paragraph, to cause the given ball 114 or 124 to be retained against the ribs 115 or 125.

Although operation of the pump-valving assembly 101 is pulsatile in nature, the flow in the chamber 102 is always in a uniform direction (in this figure, clockwise). Fluid enters the chamber 102 ultimately from the inlet port 111 and leaves the chamber 102 ultimately through the outlet port 121. This flow produces clockwise motion of the fluid in the chamber 102. The clockwise motion is triggered at least in part by configuring the geometry of the pump-valving assembly 101 to introduce tangential flow of fluid from the inlet port 111 into the chamber 102. Additionally, the large change in volume of the chamber 102, caused by the diaphragm (not shown), in the course of pumping causes fluid to undergo multiple revolutions in the chamber 102 over each stroke of the diaphragm 202. The fluid motion produces what we call a "fluidic flywheel" 103, wherein the inertia of the fluid rotating in the chamber 102 engages with fluid entering from the inlet port 111 and thus continues the fluidic flywheel. Without the fluidic flywheel 103, in-flowing fluid would encounter static resistance of fluid already in the chamber 102. The fluidic flywheel 103 produces a relatively smooth flow of fluid through the pump from end to end.

The pump-valving assembly 101 includes a fluid inflow transition region 117 protruding into the chamber 102, and a fluid outflow transition region 127 protruding from the chamber 102. These transition regions 117 or 127 mediate between the circular flow in the chamber 102 and the linear flow in the tapered tracts 116 or 126, respectively. The transition region 117 has the principal function of smoothly establishing circular flow in the chamber 102 and does so by conducting the fluid along a path that is roughly tangential to an internal circumference of the chamber 102. In contrast, the transition area 127 has the somewhat more complex function of allowing fluid to smoothly exit from the fluidic flywheel in the chamber 102 and achieve a transition to linear flow in the third tapered tract 126 to enable flow through the outlet port 121, and does so by providing a channel, beginning in the chamber 102, of gradually increasing width.

Figure 4:
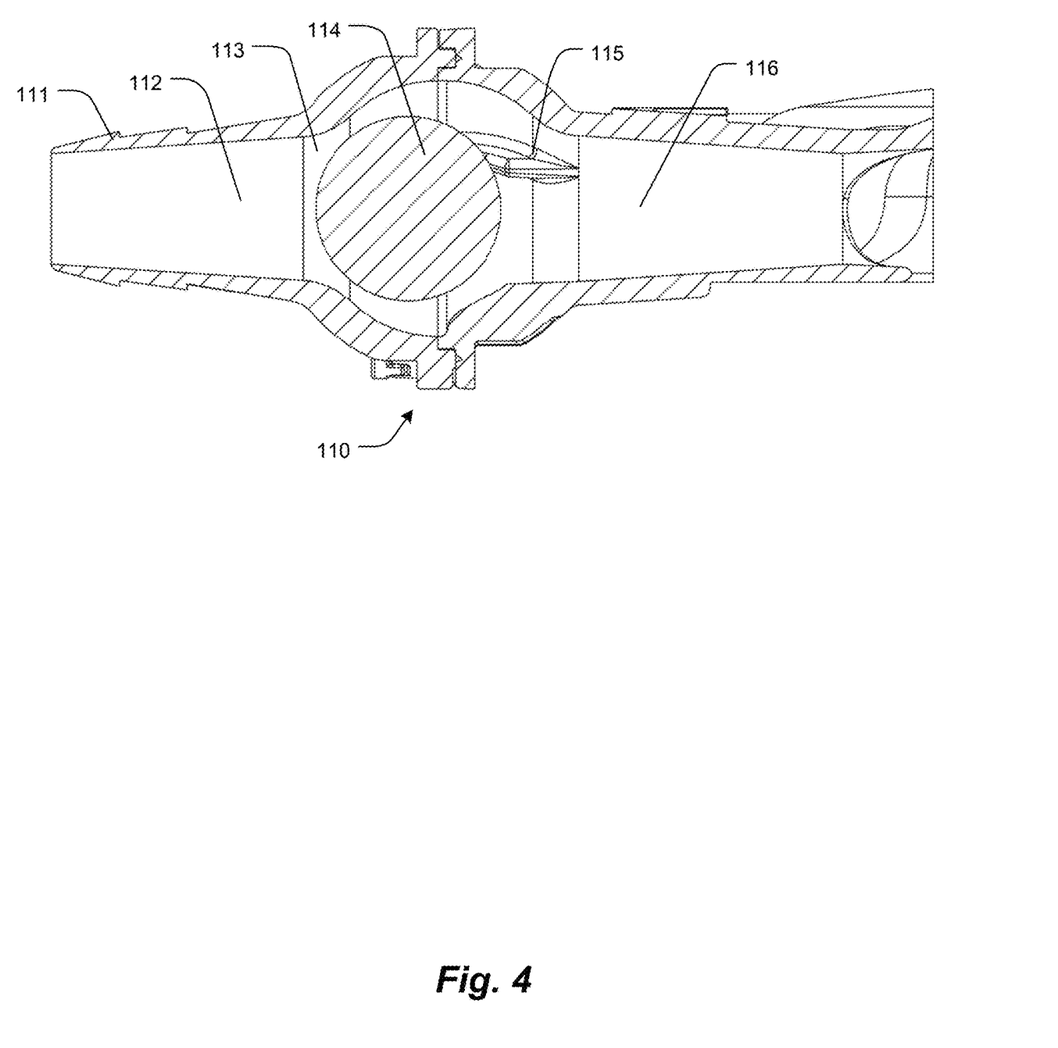
FIG. 4 is a vertical section of the inlet ball check valve assembly 110 of the embodiment of FIG. 1 wherein the pump-valving assembly 101 is in a transition mode between the diastolic and systolic modes and the inlet ball 114 is in an unseated position.

FIG. 4 is a vertical section of the inlet ball check valve assembly 110 of the embodiment of FIG. 1 wherein the pump-valving assembly 101 is in a transition mode between the diastolic and systolic modes and the inlet ball 114 is in an unseated position. During transition mode there is a slight reversal of flow until the inlet ball 114 settles against the inlet seat 113.

Figure 5:
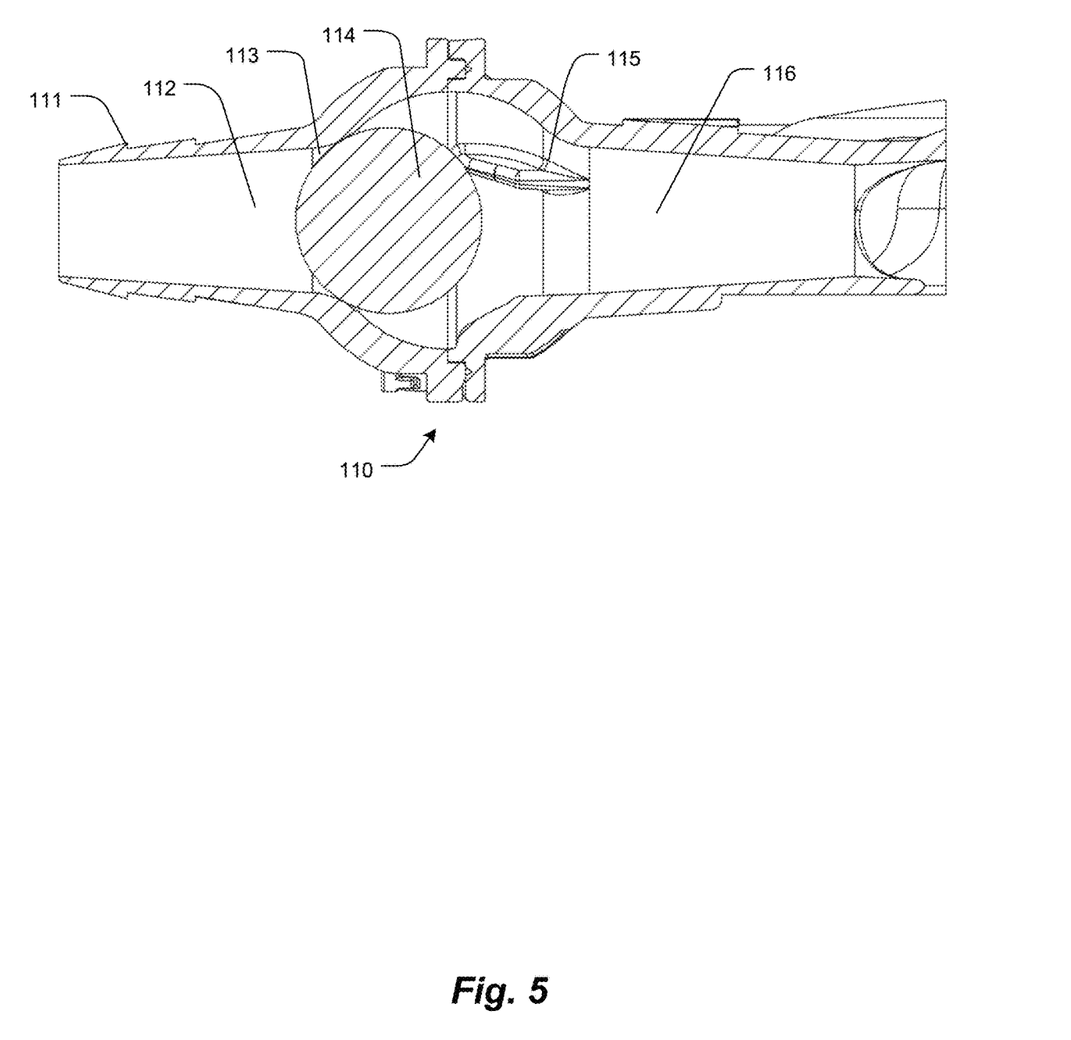
FIG. 5 is a vertical section of the inlet ball check valve assembly 110 of the embodiment of FIG. 1 wherein the pump-valving assembly 101 is in systole mode in which the chamber 102 is being emptied and the inlet ball 114 is in the emptying position.

FIG. 5 is a vertical section of the inlet ball check valve assembly 110 of the embodiment of FIG. 1 wherein the pump-valving assembly 101 is in systole mode in which the chamber 102 is being emptied and the inlet ball 114 is in the emptying position. The positive pressure created by the diaphragm (not shown) pushing towards the chamber 102 as it is emptying causes the inlet ball 114 in the inlet ball check valve assembly 110 to settle against inlet seat 113, so as to prevent fluid flow from the chamber 102 back into the inlet port 111.

Figure 6:
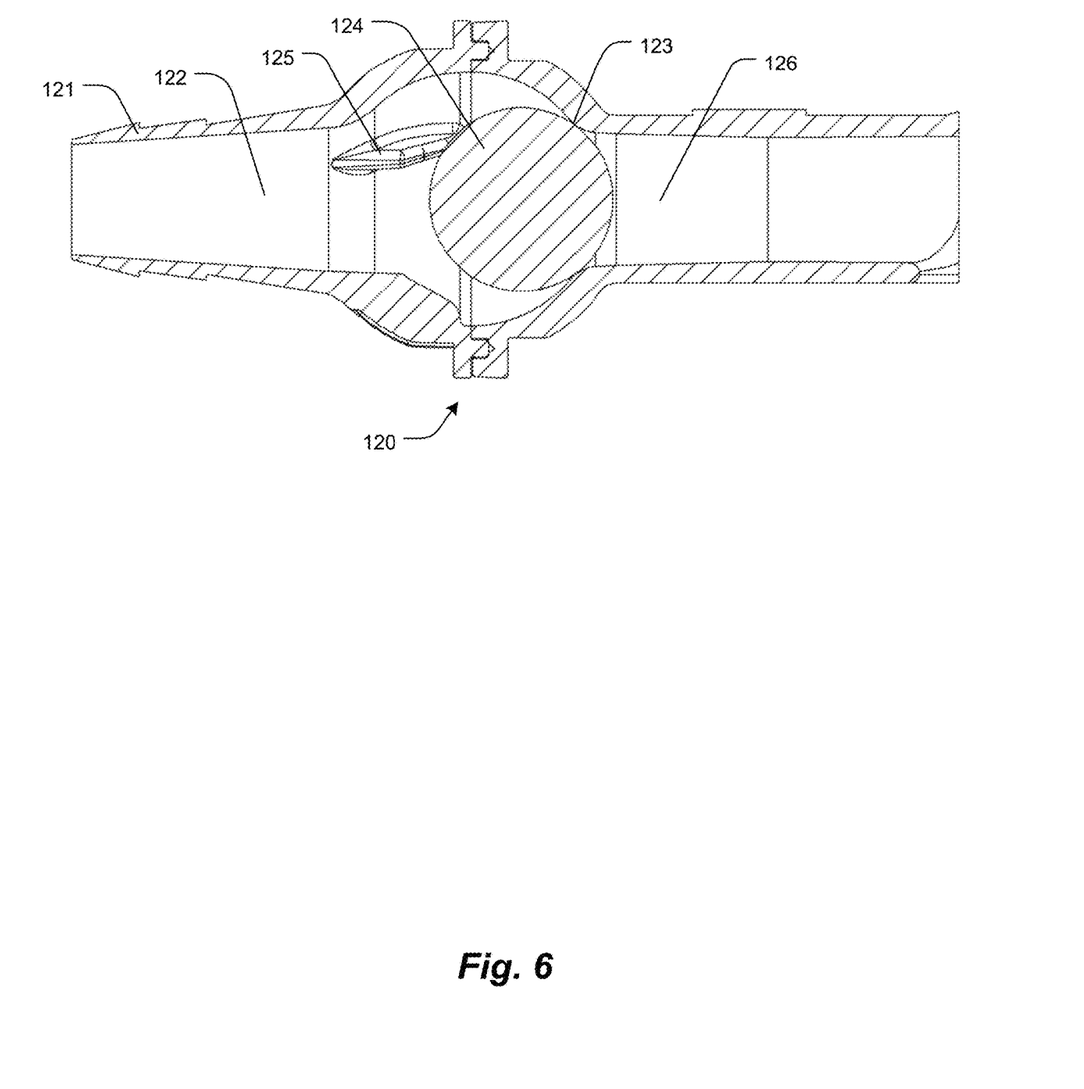
FIG. 6 is a vertical section of the outlet ball check valve assembly 120 of the embodiment of FIG. 1 wherein the pump-valving assembly 101 is in diastole mode in which the chamber 102 is being filled and the outlet ball 124 is in the filling position.

FIG. 6 is a vertical section of the outlet ball check valve assembly 120 of the embodiment of FIG. 1 wherein the pump-valving assembly 101 is in diastole mode in which the chamber 102 is being filled and the outlet ball 124 is in the filling position. The negative pressure created by the diaphragm (not shown) pulling away from the chamber 102 while it is filling causes the outlet ball 124 in the outlet ball check valve assembly 120 to settle against the outlet seat 123, so as to prevent fluid flow from the outlet port 121 back into the chamber 102.

Figure 7:
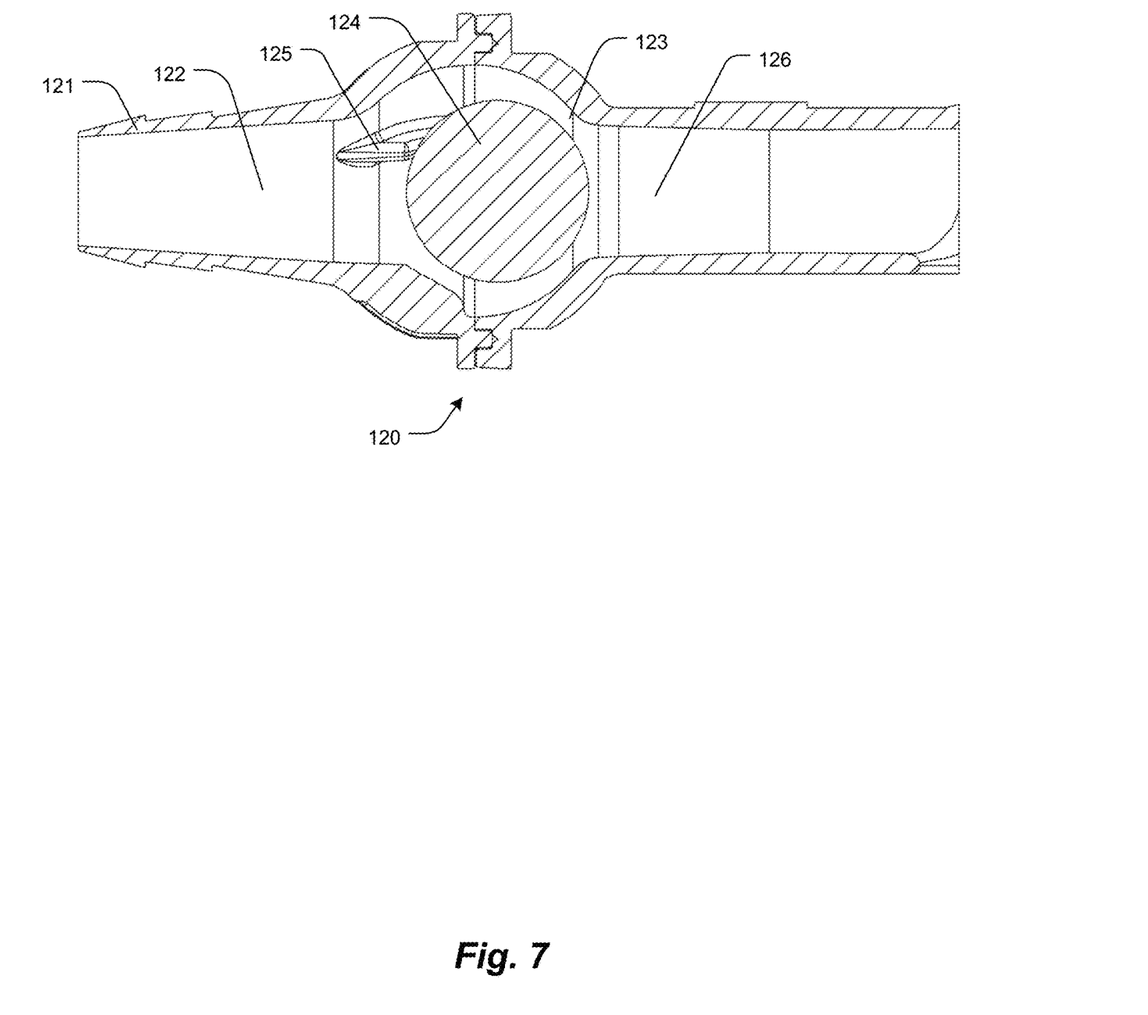
FIG. 7 is a vertical section of the outlet ball check valve assembly 120 of the embodiment of FIG. 1 wherein the pump-valving assembly 101 is in a transition mode between the diastolic and systolic modes and the outlet ball 124 is in an unseated position.

FIG. 7 is a vertical section of the outlet ball check valve assembly 120 of the embodiment of FIG. 1 wherein the pump-valving assembly 101 is in a transition mode between the diastolic and systolic modes and the outlet ball 124 is in an unseated position. During transition mode there is a slight reversal of flow until the outlet ball 124 settles against the outlet seat 123.

Figure 8:
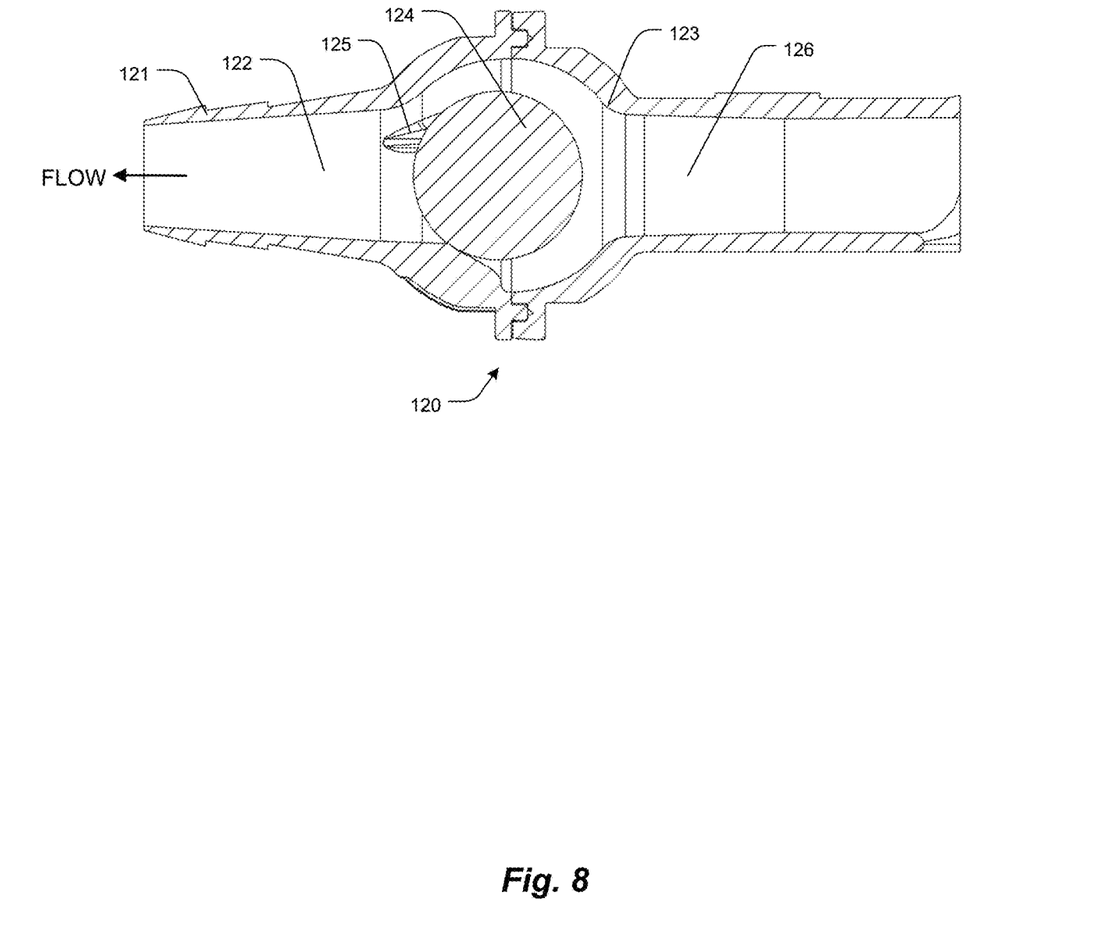
FIG. 8 is a vertical section of the outlet ball check valve assembly 120 of the embodiment of FIG. 1 wherein the pump-valving assembly 101 is in systole mode in which the chamber 102 is being emptied and the outlet ball 124 is in the emptying position.

FIG. 8 is a vertical section of the outlet ball check valve assembly 120 of the embodiment of FIG. 1 wherein the pump-valving assembly 101 is in systole mode in which the chamber 102 is being emptied and the outlet ball 124 is in the emptying position. The positive pressure created by the diaphragm (not shown) pushing towards the chamber 102 as it is emptying causes the outlet ball 124 in the outlet ball check valve assembly 120 to settle against the outlet ribs 125, so as to create gaps between the outlet ball 124 and the fourth tapered tract 122 and allow fluid to flow into the fourth tapered tract 122 and then exit the outlet port 121.

Figure 9:
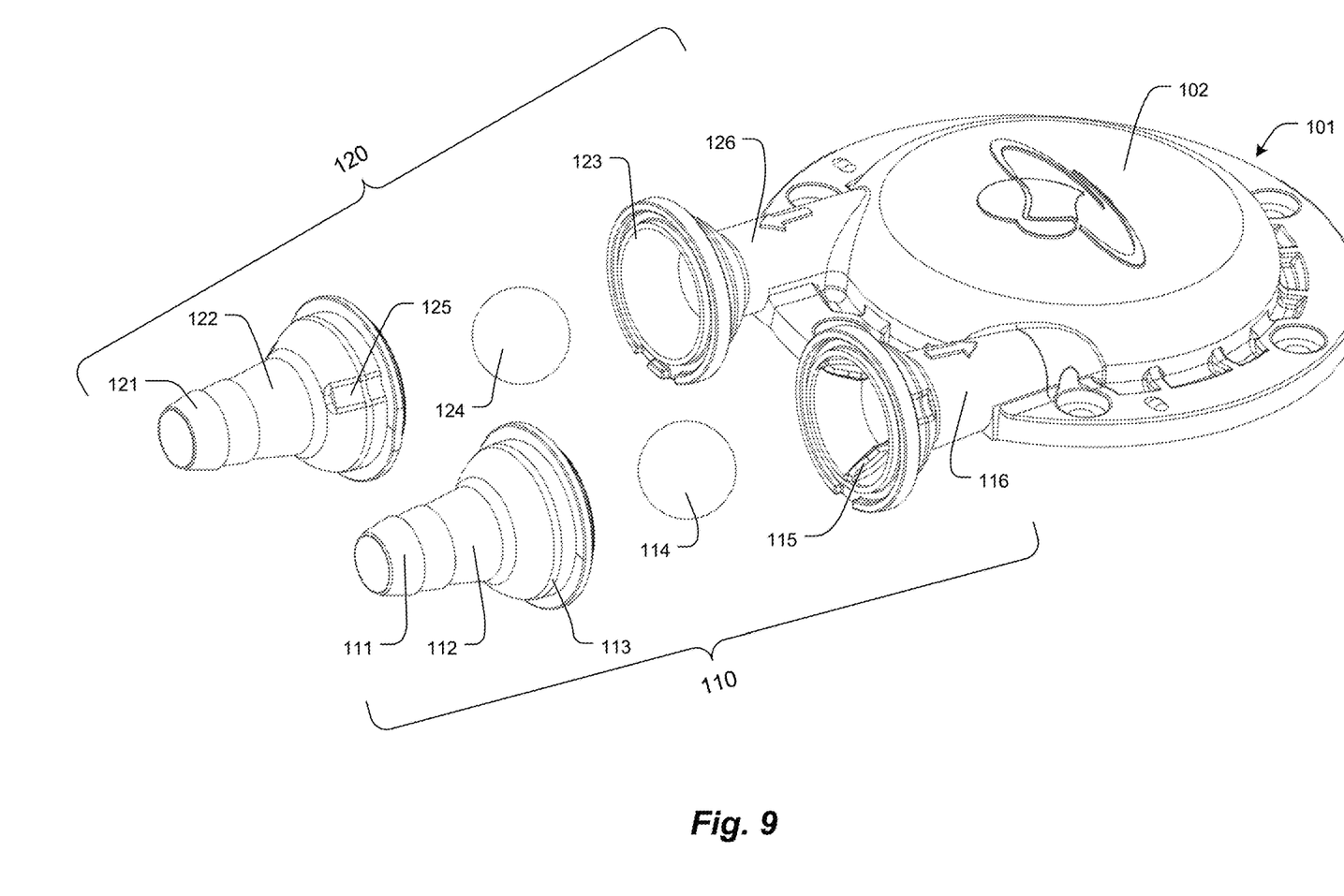
FIG. 9 is an exploded perspective view, from above, of the pump-valving assembly 101 of FIG. 1.

FIG. 9 is an exploded perspective view, from above, of the pump-valving assembly 101 of FIG. 1 showing the pump-valving assembly 101, the chamber 102 (here covered), the inlet port assembly 110, the inlet port 111, first tapered tract 112, inlet seat 113, inlet ball 114, the inlet ribs 115, the second tapered tract 116, outlet port assembly 120, the outlet port 121, the fourth tapered tract 122, the outlet seat 123, the outlet ball 124, the outlet ribs 125, and the third tapered tract 126. The diaphragm (not shown) is attached around the circumference of the bottom of the chamber 102, pushing up towards the chamber 102 in systole mode and pulling down away from the chamber 102 in diastole mode. In the pulsatile pumping of blood, although it might be thought that discontinuities in fluid flow may be useful, we have found generally that discontinuities in flow are undesirable. The pump of the present embodiment includes a number of features to reduce or eliminate such discontinuities. In particular, the tapered tracts 112, 116, 122, and 126 are configured to reduce turbulence in inflow leading to, over, and beyond the inlet ball 114 and similarly in outflow leading to, over, and beyond the outlet ball 124.

Figure 10A:
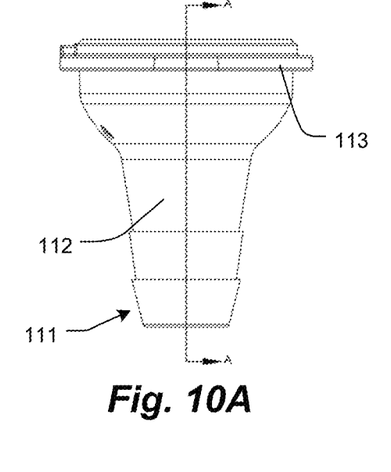
FIG. 10A is a side view of the inlet port 111 of the embodiment of FIG. 1.

FIG. 10A is a side view of the inlet port 111 of the embodiment of FIG. 1.

Figure 10B:
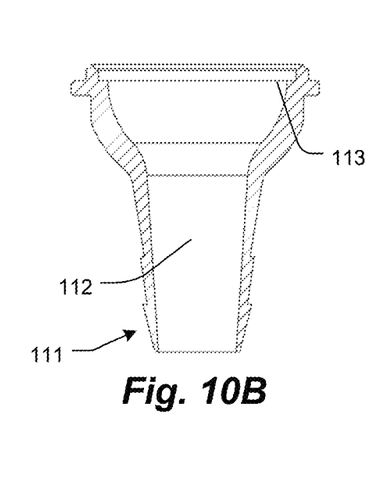
FIG. 10B is a vertical section of the inlet port 111 of FIG. 10A taken through the plane A-A.

FIG. 10B is a vertical section of the inlet port 111 of FIG. 10A taken through the plane A-A showing the first tapered tract 112, and the inlet seat 113 against which the inlet ball 114 rests to occlude flow when the pump-valving assembly 101 is in systole mode.

Figure 10C:
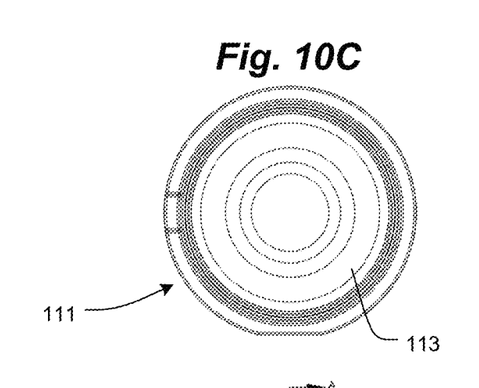
FIG. 10C is an end view of the inlet port 111 of FIG. 10A.

FIG. 10C is an end view of the inlet port 111 of FIG. 10A showing the first tapered tract 112 and the inlet seat 113.

Figure 10D:
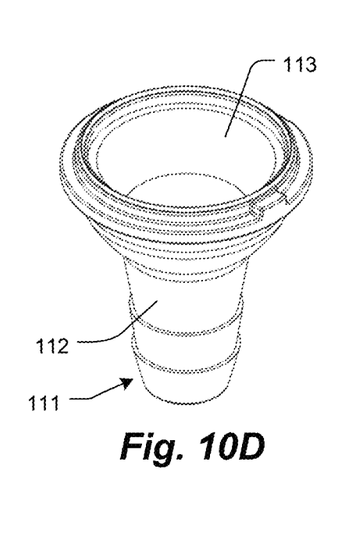
FIG. 10D is a perspective view of the inlet port 111 of FIG. 10A.

FIG. 10D is a perspective view of the inlet port 111 of FIG. 10A.

Figure 11A:
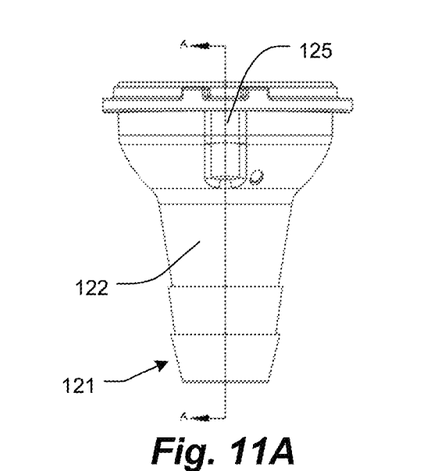
FIG. 11A is a side view of the outlet port 121 of the embodiment of FIG. 1.

FIG. 11A is a side view of the outlet port 121 of the embodiment of FIG. 1.

Figure 11B:
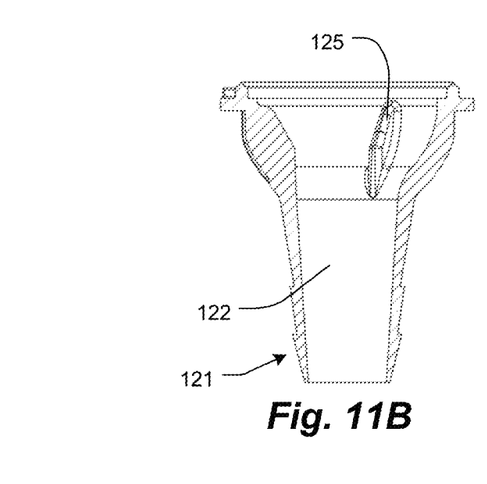
FIG. 11B is a vertical section of the outlet port 121 of FIG. 11A taken through the plane A-A.

FIG. 11B is a vertical section of the outlet port 121 of FIG. 11A taken through the plane A-A showing the fourth tapered tract 122, and the outlet ribs 125 that create gaps that allow normal fluid flow when the pump-valving assembly 101 is in systole mode.

Figure 11C:
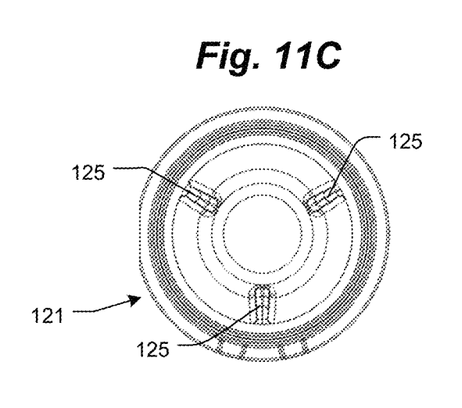
FIG. 11C is an end view of the outlet port 121 of FIG. 11A.

FIG. 11C is an end view of the outlet port 121 of FIG. 11A showing the fourth tapered tract 122, and the outlet ribs 125.

Figure 11D:
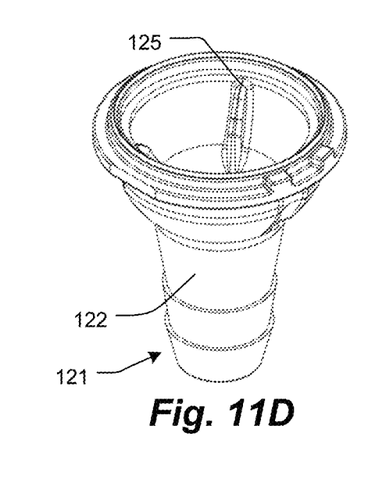
FIG. 11D is a perspective view of the outlet port 121 of FIG. 11A.

FIG. 11D is a perspective view of the outlet port 121 of FIG. 11A.

The structure of a pulsatile pump in accordance with various embodiments of the present invention can usefully reflect attributes of the human heart. The human heart is preload sensitive—the heart cannot "pull" blood into the left ventricle; it can only allow the blood available to flow naturally into the ventricle. The human heart is also afterload sensitive in that it is responsive to the compliance and resistance in the downstream vasculature and doesn't exert excess force on the blood, which could damage the vasculature. Lastly, the left ventricle cannot deliver blood that isn't in the ventricle when it contracts; there is a limited bolus of blood that it can deliver.

The pump-valving assembly 101 has similar attributes of inherent safety: it is preload and afterload sensitive, and it is limited in both the volume of blood it can deliver and the force at which it can deliver that bolus of blood. When filling, the pump-valving assembly 101 allows gravity filling from the venous reservoir, exerting minimal negative pressure. When the chamber in the pump-valving assembly 101 is emptying, the linear motor that powers the pump valving assembly is limited by design. In consequence the pump valving assembly cannot overpressure the downstream tubing or vasculature, instead delivering less than the volume of blood in the pump chamber 102, thereby only delivering as much volume as the vasculature can receive.

The pump-valving assembly 101 is analogous to a left ventricle of the human heart; the inlet ball check valve assembly 110 used in various embodiments hereof is analogous to a mitral valve; and the outlet ball check valve assembly 120 used in various embodiments hereto is analogous to an aortic valve. Like the human heart, the inlet 110 and outlet 120 ball check valve assemblies are passive and require a slight reversal of flow to close. This slight reversal of flow mimics the slight reversal that occurs when the aortic valve of the human heart closes.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A pump-valving assembly for a pulsatile fluid pump, the assembly comprising:
   a generally cylindrical pumping chamber defined by an exterior wall;
   an inlet port having an entrance and coupled to the pumping chamber; and
   an outlet port having an exit and coupled to the pumping chamber;
   a spherically shaped inlet ball check-valve assembly coupled to the inlet port through a first tapered tract, distinct from the inlet ball check-valve assembly, and to the pumping chamber through a second tapered tract, distinct from the inlet ball check-valve assembly, the second tapered tract extending directly to the exterior wall of the pumping chamber, the inlet ball check-valve assembly having an interior wall defining a spherical volume in which a discrete inlet ball is disposed, the assembly including an inlet valve seat and an ribbed inlet ball retaining region;
   a spherically shaped outlet ball check-valve assembly coupled to the pumping chamber through a third tapered tract, distinct from the outlet ball check-valve assembly, the third tapered tract extending directly to the exterior wall of the pumping chamber and to the outlet port through a fourth tapered tract, distinct from the outlet ball check-valve assembly, the outlet ball check-valve assembly having an interior wall defining a spherical volume in which a discrete outlet ball is disposed, the assembly including an outlet valve seat and an ribbed outlet ball retaining region;
   so that:
   (i) the first tapered tract expands in cross sectional area from the entrance to the inlet port to the inlet ball check valve assembly, and the second tapered tract decreases in cross sectional area from the inlet ball check valve assembly to the chamber, and the inlet ball check valve assembly gates flow between the pumping chamber and the inlet port, and
   (ii) the third tapered tract expands in cross sectional area from the chamber to the outlet ball check valve assembly and the fourth tapered tract decreases in cross sectional area from the outlet ball check valve assembly to the exit from the outlet port and the outlet ball check valve assembly gates flow between the pumping chamber and the outlet port.

2. A pump-valving assembly according to claim 1, wherein a taper of at least one of the tapered tracts is conical.

3. A pump-valving assembly according to claim 1, wherein the chamber has an outermost circumference, the pump-valving assembly further comprising an inflow transition region, coupled from the second tapered tract directly to the outermost circumference of the chamber, the inflow transition region configured to conduct fluid along a path that, at such region's entrance into the chamber, is roughly tangential to an internal circumference of the chamber, so as to smoothly establish circular fluid flow in the chamber.

4. A pump-valving assembly according to claim 1, wherein the chamber has an outermost circumference, the pump-valving assembly further comprising an outflow transition region, coupled directly from the outermost circumference of the chamber to the third tapered tract, providing a channel, beginning in the chamber, of gradually increasing width, the outflow transition region configured to allow fluid to smoothly exit from fluid rotation in the chamber to linear flow in the third tapered tract.

5. A pump-valving assembly according to claim 3, further comprising an outflow transition region, coupled directly from the outermost circumference of the chamber to the third tapered tract, providing a channel, beginning in the chamber, of gradually increasing width, the outflow transition region configured to allow fluid to smoothly exit from fluid rotation in the chamber to linear flow in the third tapered tract.

* * * * *

UNITED STATES PATENT AND TRADEMARK OFFICE
CERTIFICATE OF CORRECTION

| | |
|---|---|
| PATENT NO. | : 11,547,846 B2 |
| APPLICATION NO. | : 17/182915 |
| DATED | : January 10, 2023 |
| INVENTOR(S) | : Douglas Vincent et al. |

It is certified that error appears in the above-identified patent and that said Letters Patent is hereby corrected as shown below:

In the Claims

In Column 7, Line 57:
Replace "an ribbed" with --a ribbed--

In Column 8, Line 12:
Replace "an ribbed" with --a ribbed--

Signed and Sealed this
Thirtieth Day of April, 2024

Katherine Kelly Vidal
*Director of the United States Patent and Trademark Office*